(12) United States Patent
Sanders

(10) Patent No.: US 7,494,661 B2
(45) Date of Patent: Feb. 24, 2009

(54) METHODS FOR USING TETANUS TOXIN FOR BENEFICIAL PURPOSES IN ANIMALS (MAMMALS)

(76) Inventor: Ira Sanders, 300 E. 93rd St., Apt 43 E, New York, NY (US) 10128

( * ) Notice: Subject to any disclaimer, the term of this patent is extended or adjusted under 35 U.S.C. 154(b) by 0 days.

(21) Appl. No.: 10/312,705

(22) PCT Filed: Jun. 28, 2001

(86) PCT No.: PCT/US01/20523

§ 371 (c)(1),
(2), (4) Date: Dec. 24, 2002

(87) PCT Pub. No.: WO02/00172

PCT Pub. Date: Jan. 3, 2002

(65) Prior Publication Data

US 2004/0248188 A1    Dec. 9, 2004

Related U.S. Application Data

(60) Provisional application No. 60/214,569, filed on Jun. 28, 2000.

(51) Int. Cl.
*A61K 39/00* (2006.01)
*A61K 39/38* (2006.01)
*A61K 39/02* (2006.01)
*A61K 39/08* (2006.01)
*A61K 38/00* (2006.01)
*A61K 38/16* (2006.01)
*A01N 37/18* (2006.01)

(52) U.S. Cl. ............... 424/239.1; 424/184.1; 424/234.1; 424/247.1; 424/236.1; 514/2; 514/8

(58) Field of Classification Search .................... 514/2, 514/12, 14; 424/247.1, 239.1, 234.1, 236.1
See application file for complete search history.

(56) References Cited

U.S. PATENT DOCUMENTS

| | | | | |
|---|---|---|---|---|
| 5,562,907 A * | 10/1996 | Arnon | ...................... | 424/236.1 |
| 5,670,484 A * | 9/1997 | Binder | ........................ | 514/14 |
| 5,714,468 A * | 2/1998 | Binder | ........................ | 514/14 |
| 5,766,605 A * | 6/1998 | Sanders et al. | ........... | 424/239.1 |
| 5,897,579 A * | 4/1999 | Sanders | ........................ | 607/42 |
| 5,989,545 A * | 11/1999 | Foster et al. | ............. | 424/183.1 |
| 6,087,327 A * | 7/2000 | Pearce et al. | ..................... | 514/2 |
| 6,447,785 B1 * | 9/2002 | Donovan | ................. | 424/239.1 |
| 6,447,787 B1 * | 9/2002 | Gassner et al. | ........... | 424/247.1 |
| 6,464,986 B1 * | 10/2002 | Aoki et al. | ................ | 424/239.1 |
| 6,500,436 B2 * | 12/2002 | Donovan | ................. | 424/239.1 |
| 6,524,580 B1 * | 2/2003 | Donovan | ................... | 424/94.5 |
| 6,585,970 B1 * | 7/2003 | Donovan | ................... | 424/94.5 |
| 6,716,427 B1 * | 4/2004 | Donovan | ................... | 424/94.5 |
| 6,740,321 B1 * | 5/2004 | Donovan | ................... | 424/94.6 |
| 6,743,424 B1 * | 6/2004 | Donovan | ................... | 424/94.5 |
| 2002/0037833 A1 * | 3/2002 | Donovan | ........................ | 514/2 |
| 2002/0086036 A1 * | 7/2002 | Walker | ..................... | 424/236.1 |
| 2002/0094339 A1 * | 7/2002 | Brin et al. | ................. | 424/247.1 |
| 2003/0138640 A1 * | 7/2003 | Rische et al. | ............... | 428/446 |
| 2003/0202990 A1 * | 10/2003 | Donovan et al. | ......... | 424/239.1 |
| 2004/0018212 A1 * | 1/2004 | Aoki et al. | ............... | 424/239.1 |
| 2004/0018214 A1 * | 1/2004 | Aoki et al. | ............... | 424/239.1 |
| 2004/0028706 A1 * | 2/2004 | Aoki et al. | ............... | 424/239.1 |
| 2004/0037895 A1 * | 2/2004 | Zhu | ........................... | 424/697 |
| 2004/0086531 A1 * | 5/2004 | Barron | ..................... | 424/239.1 |
| 2004/0086532 A1 * | 5/2004 | Donovan | ................. | 424/239.1 |
| 2004/0115139 A1 * | 6/2004 | Katz et al. | ..................... | 424/50 |
| 2004/0248188 A1 * | 12/2004 | Sanders | ....................... | 435/7.1 |

FOREIGN PATENT DOCUMENTS

| | | | |
|---|---|---|---|
| WO | WO 95/28171 A1 * | 10/1995 | |
| WO | WO 00/24419 A1 * | 5/2000 | |
| WO | WO 03/000193 A2 * | 1/2003 | |
| WO | WO 2004/048519 A2 * | 6/2004 | |
| WO | WO 2004/076634 A2 * | 9/2004 | |

OTHER PUBLICATIONS

Habermann, E. et al. 1988. Tetanus toxin and Botulinum A and C neurotoxins inhibit noradrenaline release from cultured mouse brain. J. Neurochem. 51(2): 522-527.*
Kryzhanovskil et al, Bull. Exp. Biol. Med., 1975, 77/7:732-736.*
Bizzini et al, Toxicon., 1988, 26/3:309-318.*
Kitamura et al, Biochimica et Biophysica Acta, 1999, 1441:1-3.*
Fezza et al, Ophthalmic Plastic and Reconstructive Surgery, 2000, 16/2:101-113.*
Li et al, JBC, Aug. 2001, 276/33:31394-31401.*
Williamson et al, JBC, Aug. 1999, 274/35:25173-25180.*
Grangette et al, Vaccine, 2002, 20:3304-3309.*
Kryzhanovskii et al, Bull. Exp. Biol. Med., 1974, 76/9:1030-1033.*
Ricker et al, J. Neurol. 1974, 207:155-163.*
Sherwin et al, Journal of Voice, 1994, 8/1:65-69.*
Horn et al, Journal of Comparative Neurology, 2000, 420:19-34.*
Kryzhanovskii et al, Bull. Exp. Biol. Med., 1975, 78/11:1234-1237.*
Yavin et al, JBC, 1981, 256/13:7014-7022.*
Gonzalez-Forero et al, J. Neuroscience, Jan. 12, 2005, 25/2:429-417.*

(Continued)

Primary Examiner—N. M Minnifield
(74) Attorney, Agent, or Firm—Omri M. Behr

(57) ABSTRACT

Methods of using tetanus toxin to modulate or control neural functions or nonneural cellular activities at selected sites in animals, particularly in mammals, and more particularly in humans, are provided. Pharmaceutical formulations to modulate neural functions or non-neural cellular activities of an animal at selected sites in animals, particularly in mammals, and more particularly in humans are also provided. Uses of tetanus toxin in preparation of medicaments for methods of treating clinical disorders or symptoms of animals, particularly mammals and more particularly humans are also provided.

30 Claims, No Drawings

OTHER PUBLICATIONS

Gonzalez-Forero et al, J. Neurophysiol., 2003, 89:1878-1890.*
Ahnert-Hilger et al, Progress in Neurobiology, May 1995, 46/1:83-96.*
Gonzalez-Forero et al, NeuroReport, Mar. 26, 2001, 12/4:753-756.*
Price et al, Science, May 30, 1975, 188:945-947.*
Habermann et al, J. Neurochemistry, 1998, 51:522-527.*
Kryzhanovskii et al, Bull. Exp. Biol. Med., Jan. 1975, 77/7:732-736.*
Matsuda et al, Biochemical and Biophysical Research Communications, Jan. 29, 1982, 104/2:799-805.*
Rabasseda et al, Toxicon, 1988, 26/4:329-336.*
Aguilera et al, J. Neurochemistry, 1991, 56:733-738.*
Bigalke et al, Naunyn-Schmiedeberg's Arch. Pharamcol., 1981, 316:544-251.*
Korolkiewicz et al, Pharmacological Research, 1998, 37/6:477-483.*
Kryzhanovskii et al, Bulletin of Exptal. Biology and Medicine, 1961, 52/11:35-43.*
Sanofi Pasteur, Inc. Product Information, Tetanus Toxoid Adsorbed, 2005, pp. 1-5.*
Pellizzari et al, Phil. Trans. R. Soc. Lond., 1999, 354:259-268.*
Rethy et al, Lancet, 1997, 350/9090:1518.*
Ahnert-Hilger et al, Progress in Neurobiology, 1995, 46:83-96.*
Niemann et al, Behring Institute Mitteilungen, 1991, 89:153-162 abstract only.*
Schantz et al, Microbiological Reviews, 1992, 56/1:80-99.*
Demain et al, Vaccine, 2005, 23:5420-5423.*
Turton et al, TRENDS in Biochemical Sciences, 2002, 27/11:552-558.*
Grumelli et al, NeuroToxicology, 2005, 26:761-767.*
Dokmetjian et al, Vaccine, 2000, 18:2698-2703.*
Gaber et al, J. R. Soc. Med., 2005, 98:63.*
Journal of Biological Standardization, 1973, 1, 203-213.*
Dolimbek et al, Immunol. Invest., Aug.-Nov. 2002, 31(3-4):247-262 Abstract only.*

* cited by examiner

US 7,494,661 B2

METHODS FOR USING TETANUS TOXIN FOR BENEFICIAL PURPOSES IN ANIMALS (MAMMALS)

This application is a 371 of PCT/US01/20523 filed on 28 Jun. 2001 claiming priority of Provisional Application 60/214,569 filed 28 Jun. 2000.

FIELD OF INVENTION

The invention relates broadly to methods of modulating a neural function of an animal, including a mammal, at a selected site. The invention also relates broadly to methods of modulating other nonneural cellular activity of an animal at a selected site. The invention also encompasses pharmaceutical formulations for modulating a neural function or a non-neural cellular function of an animal at a selected site. The invention also relates to the use of tetanus toxin in the preparation of medicaments for methods of treating clinical disorders or symptoms of an animal.

BACKGROUND OF THE INVENTION

The Clostridial neurotoxins are the most potent toxins known to man. When *Clostridium botulinum* bacteria are ingested orally they produce botulinum toxin (BT). BT is absorbed from the gastrointestinal tract and is transported by the circulatory system to muscles throughout the body. The BT binds to and blocks neuromuscular transmission from motor neurons causing a fatal paralysis known as botulism.

An unusual attribute of the BT is that its action lasts for months but the patient completely recovers. As a result of this unique attribute, BT has many clinical uses. At present, the local injection of small doses of BT is used to decrease or block muscle activity in a wide variety of clinical motor disorders. More recently, the use of BT has been extended to block autonomic nerves that use the same neurotransmitter used in neuromuscular transmission, namely, acetylcholine.

The other class of Clostridial bacteria is *Clostridia tetani*. These bacteria infect wounds and produce tetanus toxin. Tetanus toxin (TT) is released from the site of the infection and is distributed by the circulatory system to motor neurons throughout the body. Instead of acting on the motor neurons directly, the tetanus toxin is transported to the central nervous system where it blocks neurons that normally inhibit motor neuron activity. The result is a gradually increasing tone in affected muscles that culminates in a widespread spasm of muscles throughout the body. The resulting spastic paralysis is often fatal with death resulting from respiratory depression or circulatory collapse.

Tetanus has been recognized as a disorder since antiquity and it is still common throughout the world. Many countries routinely vaccinate children with tetanus toxoid, an attenuated form of the toxin that is exposed to formaldehyde to remove its biological activity while retaining its antigenicity. Tetanus toxoid is the largest biologic product in the pharmaceutical industry.

The action of the tetanus toxin lasts from weeks to months. Once TT enters into and blocks neurotransmission from neuron synapses the process is irreversible. Recovery of function requires the growth of a new process from the neuron that eventually reconnects to the motor neuron and restores the inhibitory activity back to normal levels. The time required for this recovery varies from weeks to up to five months (Struppler, A., et al. Arch Neurol, 8, 162-1782, (1963)).

The extremely broad range of TT actions allows it to either excite or inhibit practically any part of the nervous system for prolonged periods of time with a single injection. Since the nervous system closely monitors and controls nearly every organ and physiological function it has been unexpectedly found that TT can have extensive beneficial utility for the treatment or amelioration of a wide variety of clinical disorders.

Tetanus is a systemic intoxication by the tetanus toxin which is characterized by progressive spastic contraction of the skeletal muscles and overactivity of the autonomic nervous system that is often fatal.

Other than the systemic disorder three lesser known variants or tetanus are known. These are neonatal, cephalic and local tetanus. Neonatal tetanus is a fatal intoxication of newborn babies that is manifest as a systemic flaccid paralysis. Cephalic tetanus occurs on the face and combines a localized paralysis, most often of the facial nerve, with a surrounding area of muscle spasm (Dastur, F. D., et al., Journal Of Neurology, Neurosurgery And Psychiatry 40(8), 782-6 (1977)). Local tetanus is an isolated spasm of a muscle group or limb that may progress to systemic tetanus or resolve over weeks to months (Johns Hopkins Medical Journal, 149(2) 84-8, (1981); Jain, S., et al., Journal Of Neurology, 228(4), 289-93, (1982)).

The tetanus toxin has some unique properties that have made it perhaps the most studied of all biological toxins. For example, the tetanus toxin binds to all types of neurons. Although its primary affinity is to bind to motor neurons, TT also binds to neurons of the autonomic nervous system and sensory neurons (Stockel, K., et al., Brain Research, 99, 1-16 (1975)). In contrast, the botulinum toxins principally bind to motor neurons.

Tetanus toxin requires multiple specific steps to cause its effects in neurons. These steps include (i) peripheral binding; (ii) internalization; (iii) retrograde transport; (iv) central binding; and (v) transmembrane internalization.

In peripheral binding the toxin binds to the surface of the cell. TT binds to the presynaptic membrane of practically all neurons. In addition it also binds to the membrane of the neuron's axon. The receptors to which TT binds are a class of molecules known as gangliosides. BT also binds to gangliosides, however BT appears to bind principally to those on the presynaptic membrane of cholinergic neurons, whereas TT binds to the pre-synaptic membrane of most if not all neurons.

In the internalization step the toxin is brought into the cell. TT is brought into the neuron by the process of forming a vesicle. While TT remains inside the vesicle, although physically inside the neuron, the toxin is separated from the cytoplasm of the neuron by a membrane. In contrast, BT is thought to require a second molecule on the presynaptic membrane to bind to before being internalized. After BT binds to the second molecule it passes through the cell membrane directly into the cytoplasm, which is why it exerts its effect at the peripheral presynaptic membrane.

During the retrograde transport the vesicles containing TT are transported to the cell body in the central nervous system. The vesicle then fuses with the cell membrane of the cell body or its dendrites thereby depositing TT into the extracellular space between the motor neuron on the processes of other neurons synapsing onto the motor neuron (Hilbig, G., K. O. Raker, et al., Naunyn-Schmiedebergs Archives Of Pharmacology, 307(3), 287-90, 1979.

In the central binding step TT can bind to all neurons. However, TT has a much greater affinity for the inhibitory neurons. At low concentrations, tetanus has greater affinity for the neurons that use the inhibitory neurotransmitters GABA and glycine (Montecucco, C. et al., Q Rev Biophys, 28(4), 423-72, (1995)). At higher concentrations, it blocks all neurotransmitters. Finally, tetanus toxin has a local effect on axons that causes a local block of the propagation of action potentials. The mechanism for this is unknown but the result is similar to the action of a local anesthetic.

During the transmembrane internalization, once the toxin binds to a second neuron it is internalized and produces its toxic effect.

The primary mechanism of action of TT is to block the release of vesicles from a cell. In neurons these vesicles contain neurotransmitters. The proteins that are involved in the attachment of a vesicle to the inner membrane of a cell are the SNARE (synaptosome associate protein receptor) family of proteins. These proteins are part of the mechanism by which intracellular vesicles dock to cell membranes and release their contents. Specifically, tetanus toxin cleaves VAMP (vesicle associated membrane protein). Botulinum toxins A and E cleave SNAP-25; and botulinum toxin C cleaves SNAP-25 and syntaxin; tetanus toxin and botulinum neurotoxins type B, D, F and G cleave VAMP, an integral protein of the neurotransmitter containing synaptic vesicles.

The mechanism of vesicle release is common to all cells from yeast to the cells of humans. The TT molecule is composed of a heavy chain that is responsible for its specific binding and transport properties, and a light chain that actually performs the catalytic action on the VAMP protein. There are a few non-neuronal cells in which TT is capable of entering and performing its action and these will be discussed in the examples.

Multiple experiments have shown that even if TT is incapable of binding and entering into a type of cell it can be inserted by a variety of mechanisms. Once inside the cell TT cleaves VAMP and disables vesicle release. Different cells use the mechanism to secrete hormones, neuropeptides, lysozyme proteins, and other substances. Whatever specific substance is secreted by the cell it will be blocked by TT if secretion requires the use of VAMP protein.

Cells can be made susceptible to TT by placing gangliosides onto the external surface of the cell membrane. Another manner of inserting TT into cells is by chemically combining the TT, or at a minimum its light chain, with a second molecule that is capable of binding to the cell. In addition the TT can be inserted by micro injection using micropipettes, pressure injection, by incorporation into lysosomes, or by temporarily making the cell membrane permeable to TT.

Motor neurons are the primary target of TT toxicity. Motor neurons refer to cholinergic neurons that innervate the large extrafusal muscle fibers of skeletal muscle. Within skeletal muscle are smaller intrafusal muscle fibers and these are innervated by a smaller cholinergic motor neuron called a gamma neuron. These also are intoxicated by TT. Finally, smooth muscle is also innervated by cholinergic neurons. Although the vast majority of these neurons are cholinergic and are formally considered part of the autonomic nervous system they are sometimes grouped with the other motor neurons for discussion because they have certain biologically similar properties. TT has been shown to bind to and intoxicate the motor neurons of smooth muscles in the same manner as it does to striated muscle fibers.

It should be noted that at high doses TT can cause a flaccid paralysis by blocking motor neuron activity both in the periphery, at the neuromuscular junction, and centrally, by blocking all afferent input from both excitatory and inhibitory axons. Which of the two areas predominate in a given case of intoxication is dependent on where the TT infection is and how it progresses.

In cephalic tetanus all three actions of TT can occur together. At the site of infection the muscle exhibits a flaccid paralysis as TT levels are high and the neuromuscular synapses are blocked directly. In addition high levels of the toxin are transported back to the brainstem to block central nervous system input. However at variable distances surrounding the site of infection the concentration of TT falls until areas are seen in which muscles are in spasm (Dastur, F. D., et al., Journal Of Neurology, Neurosurgery And Psychiatry 40(8), 782-6 (1977)).

Tetanus toxin can be measured by weight or, more commonly, by biological assay. The effective dose of tetanus is measured in units, the amount of tetanus toxin that is lethal to 50% of mice when injected subcutaneously. A unit of tetanus toxin may range between 0.1 to 100 ng of toxin per kg of mouse body weight. In the mouse hemi diaphragm assay, a 500 times higher dose of tetanus toxin is needed to cause a flaccid paralysis (Bigalke, H. et al., Naunyn Schmiedebergs Arch Pharmacol, 312(3), 255-63, (1980)). Therefore at equivalent weights tetanus toxin would be expected to cause a spastic paralysis while botulinum toxin causes a flaccid paralysis.

Tetanus toxin has the same effects on autonomic neurons as it does on motor neurons (Abboud, F. M., Hypertension, 4 (3 Pt 2), 208-25, (1982)). In systemic tetanus excitation of the autonomic nervous system is prominent and manifest by such symptoms as high blood pressure (Toriya, Y., I. et al. Endodontics And Dental Traumatology, 13 (1), 6-12, (1997)), erratic changes in blood pressure, high fever, and profuse sweating. Therefore, low concentrations result in increased autonomic tone with physiological changes resulting in all organs affected.

The autonomic nervous system is divided into the parasympathetic system which uses acetylcholine as its neurotransmitter and the sympathetic systems which uses epinephrine as the neurotransmitter. In both the parasympathetic and sympathetic systems neurons do not reach the entire distance from the central nervous system to the peripheral organ. Instead the distance requires two neurons with a synapse somewhere in the periphery. In the sympathetic system these are grouped together in a limited number of large ganglia located near the spinal column. In the parasympathetic organ the synapse is usually located in a smaller ganglia near the target organ. In both systems the neurotransmitter used in the ganglia synapses is always acetylcholine.

Although the peripheral neurons of the sympathetic nervous system may all use norepinephrine as their neurotransmitter; the response of the target organ cells is dependent on the type of receptor. There are three types of adrenergic receptors: alpha (smooth muscle contraction), betal (cardiac acceleration and fatty acid mobilization) and beta 2 (smooth muscle relaxation). Note that the exact effect of norepinephrine may be entirely opposite on different muscles based on the type of receptors found on the surface. Much of this information is known for most organs that are clinically relevant.

The presence of ganglia and multiple neurotransmitters increases the complexity of the autonomic system relative to the motor system. An organ is usually innervated by both parasympathetic and sympathetic neurons and they usually have opposite actions on the target. Therefore an understanding of the anatomy and physiology of the target organ is important in planning the location of a TT injection so that the desired effect is to be achieved.

Sensory neurons can also be blocked by tetanus toxin. Sensory neuropathies are part of the symptom complex of clinical tetanus. One aspect of Clostridial tetanus infection is that pain and inflammation at the site of infection are much lower then would be expected in such serious infections. Therefore, it is believed that TT blocks sensory neurons.

In addition to neurotransmitters, which are usually used to directly communicate with other neurons through synaptic connections, neurons release neuropeptides from motor, sensory and autonomic nerves (SP, substance P; NKA, neurokinin A; CGRP, calcitonin gene-related peptide; NPY, neuropeptide Y, interleukins and growth factors). These neuropeptides have many different effects but one of the most important is vasodilatation and inflammation. (Bigalke, H. et al., Naunyn Schmiedebergs Arch Pharmacol, 312(3), 255-63, (1980)). These neuropeptides are released by the same vesicle mechanism as neurotransmitters and therefore can be blocked by TT.

The SNARE proteins and the vesicle release mechanism are used by cells for purposes other then the release of neurotransmitters. In fact, the release of practically all cellular secretions depends on this mechanism. These include the release of hormones, enzymes, and inflammatory modulators, mucus secretions from respiratory, digestive and urinary glands, and inflammatory modulators from nerves and white blood cells (Alexander, E. A., et al., American Journal of Physiology, 273 (6 Pt 2), F1054-7 (1997)). Cells known to internalize tetanus toxin include macrophages, endocrine cells, and renal cells (Huet de la Tour, E., et al. Journal Of The Neurological Sciences, 40(2-3), 123-31, (1979)).

In addition to their effect on SNARE proteins, Clostridial toxins have been shown to interfere with other cell activities. For example, it can prevent actin molecules from forming into filaments. Actin is the main cellular skeleton protein involved in cell shape and movement. This action can block the contraction of muscle cells as well as stop the migration of white blood cells and possibly malignant cells also. The toxins also interfere with cell signaling. Specifically, receptors on a cell's surface respond to specific molecules by promoting a cascade of secondary proteins that in turn result in a variety of cell functions from changes in morphology to secretion.

In "Ophthalmic and Reconstructive Surgery," 16 (2), 101-13, (2000), Fezza J. P. et al. disclose the use of tetanus toxin to cause localized orbiculari oculi weakness without producing systemic tetany in immunized rabbits. Potential uses of tetanus toxin in treatment of blepharospasm and hemifacial spasm are suggested without provisions of any detailed information regarding dosage or other description useful to one skilled in the art seeking to use the tetanus toxin to treat these conditions.

U.S. Pat. No. 5,989,545 to Foster et al. describes the use of the light chain of a clostridial neurotoxin by itself or linked to other moieties as a pharmaceutical for the treatment of pain. Foster et al. do not disclose the use of the entire molecule of tetanus toxin.

U.S. Pat. No. 5,714,468 to Binder describes the use of a fragment of tetanus toxin to reduce pain in migraine headaches. U.S. Pat. No. 5,670,484 to Binder discloses a method for treatment of cutaneous cell-proliferative disorders with Botulinum toxin A and tetanus toxin. In both patents, Binder uses the same TT dosages as are used for BT. Moreover, he discourages the use of TT for beneficial purposes because he found that TT to be too toxic at the dosages disclosed in his patents.

U.S. Pat. No. 5,766,605 to Sanders et al. describes the control of autonomic nerve function in a mammal by administering to the mammal a therapeutically effective amount of Botulinum toxin. There is no disclosure of tetanus toxin.

Despite the apparent effects of neurotoxins on motor, autonomic and sensory neurons, the use of such toxins, and especially tetanus toxin in animals, including humans, has been limited and has never been used for clinical applications.

Thus, there remains a need in the medical art for methods of treating patients with tetanus toxin that can cause an increase or decrease in neural activity at selected sites of the patient. Similarly, there is still a need in the medical arts for methods using tetanus toxin to treat clinical disorders caused by improper cellular activity, such as inflammatory conditions. Further, there remains a need for pharmaceutical formulations that can be delivered to a patient to achieve clinically beneficial results or treat certain dysfunctions, while eliminating or minimizing dependence, tolerance, and side effects associated with more conventional drugs.

OBJECTS OF THE INVENTION

It is an object of the invention to provide a method of using tetanus toxin to achieve beneficial effects in animals, particularly in mammals and more particularly in humans.

It is an object of the invention to provide a treatment of neuromuscular dysfunctions in animals, particularly in mammals and more particularly in humans.

It is an object of the invention to provide a treatment of autonomic nerve dysfunctions in animals, particularly in mammals and more particularly in humans.

It is another object of the invention to control sensory functions in particularly animals, particularly in mammals and more particularly in humans.

It is an object of the invention to modulate or control neural functions in animals, particularly in mammals and more particularly in humans.

It is another object of the invention to use tetanus toxin modulate non-neural cellular activities of cells in animals, particularly in mammals and more particularly in humans.

SUMMARY OF THE INVENTION

In view of the above objects and others, the present invention is directed in part to a method of modulating a neural function of an animal at a selected site affected by target neurons, the method including administering a therapeutically effective amount of tetanus toxin to the selected site of the animal such that the tetanus toxin reversibly modulates the activity of the target neurons.

In one aspect of the present invention, a therapeutically effective amount of tetanus toxin is sufficient to cause decrease in neural activity or reversible inhibitory response of the neural activity at the selected site.

In another aspect of the present invention, the therapeutically effective amount of tetanus toxin is sufficient to cause increase in target neuron activity or an excitatory response of the neural activity at the selected site.

In another embodiment, the present invention is further directed to a method for decreasing the activity of a nerve function in an animal including administering to a selected site affecting target neurons of an animal an amount of tetanus toxin sufficient to cause a denervation of the target neurons, wherein the denervation results in a reversible inhibitory response of the nerve function at the selected site innervated by the target neurons.

In yet another embodiment, the present invention is directed to a method for increasing the activity of a nerve function in an animal comprising administering to a selected site affecting target neurons of an animal an amount of tetanus toxin sufficient to cause an excitatory response of the nerve function at the selected site innervated by the target neurons.

In another aspect, the invention is related to a method for controlling neural function in animals, particularly mammals, and more particularly humans, comprising administering to a selected site a therapeutically effective amount of tetanus toxin to control the neural function.

In certain embodiments of the present invention including each of the foregoing methods, the decrease or increase in neural activity occurs over a period of time from about one hour to about one year. In certain preferred embodiments, the decrease or increase in neural activity occurs over a period of time from about one week to about four months.

In certain embodiments of each of the foregoing methods, each of the foregoing methods includes: (i) determining the level of antibodies of tetanus toxin present in blood plasma of the animal prior to administering of any tetanus toxin; and (ii) immunizing the animal when the level of tetanus toxin is below 0.1 IU/ml. The immunizing step is performed passively or actively. The level of antibodies of tetanus toxin present in blood plasma is determined by antibody titer or any applicable other method known in the art.

In each of the embodiments of the foregoing methods the therapeutically effective amount of tetanus toxin is delivered at the selected site by injection, topical application, aerosol, or instillation into ducts or body orifices. In certain preferred embodiments of the foregoing methods the therapeutically effective amount of tetanus toxin is delivered to the target neurons encapsulated into liposomes or artificial vesicles with bi-layer lipid membranes.

In certain preferred embodiments of each of the foregoing methods, the therapeutically effective amount of tetanus toxin is suspended in a pharmaceutically acceptable carrier.

In other preferred embodiments of each of the foregoing methods, the tetanus toxin is in the form of freeze-dried powder.

In each of the foregoing embodiments of each of the foregoing methods the target neurons include motor neurons, autonomic neurons, sensory neurons or neurons of the central nervous system.

In certain embodiments of each of the foregoing methods, the activity of the target neurons is affected by inhibiting directly or indirectly the release of neurotransmitters or neuropeptides.

In certain preferred embodiments of the invention wherein the neural activity of the target neurons is reversibly inhibited or the target neurons are denervated, the therapeutically effective amount of TT is from about 100 units to about 10,000 units for the selected site.

In other more preferred embodiments wherein the neural activity of the target neurons is reversibly inhibited or the target neurons are denervated by administration of tetanus toxin, the therapeutically effective amount of TT is from about 500 units to about 5000 units for the selected site.

In other most preferred embodiments of each of the foregoing methods of reversibly inhibiting the neural activity of or denervating the target neurons, the therapeutically effective amount of TT is from about 1000 units to about 2000 units for the selected site.

In certain other preferred embodiments of each of the foregoing methods, wherein the administration of tetanus toxin results in the increase of the neural activity of the target neurons or in an excitatory response of the nerve function at the selected site innervated by the target neurons, the therapeutically effective amount of TT is from about 0.01 units to about 2000 units for the selected site. In certain more preferred embodiments of each of the foregoing methods, the therapeutically effective amount is from about 1 unit to about 10 units for the selected site. In certain most preferred embodiments of the foregoing methods, the therapeutically effective amount is from about 2 units to about 4 units for the selected site.

In certain other embodiments of each of the foregoing methods, whenever the tetanus toxin is administered at a selected site it evokes an excitatory response in target neurons associated with tissues or organs of the skeletal muscles. For these foregoing embodiments, applicable clinical disorders include without limitation sleep apnea and snoring, scoliosis, strabismus, muscle atrophy, neurologically impaired muscles including muscular dystrophy, ALS, or myasthenia gravis, decrease in muscle mass, or decrease in facial muscle tone.

In other embodiments of each of the foregoing methods, whenever the administration of TT evokes an excitatory response of neural activity in smooth muscles such as tissues or organs including without limitation lower esophageal sphincter, anal sphincter, bladder, bladder sphincter, vaginal sphincter, pyloric sphincter, upper esophageal sphincter, colon wall muscles.

In other embodiments of the invention, wherein the methods of the invention include administration of TT evoking an excitatory response of target neurons of the autonomic, parasympathetic nervous system, the selected sites include tissues or organs affecting saliva production, the organs affecting saliva production including the submandibular gland, parotid gland, sublingual gland, or minor salivary glands of the oral mucosa.

In yet other embodiments, wherein the methods of invention include administration of TT to evoke an excitatory response of target neurons of the autonomic sympathetic nervous system, the selected site comprises tissues or organs affected by nasal congestion, impotence, hair loss or hypotension.

In certain other embodiments of the foregoing methods, the tetanus toxin is administered to skeletal muscles to evoke a reversible inhibitory response at the selected sites including tissues or organs affected by spastic dysphonia, hemifacial spasm and blepharospasm, temporal mandibular join syndrome or bruxism, torticollis, neck pain, writer's cramp, limb muscle contracture, nerve regeneration within a muscle or migraine headache. The applicable skeletal muscles include vocal folds, facial muscles, masseter muscle, sternocleidomastoid muscle, trapezius muscle, forearm muscles, limb muscles, temporalis muscles and other unspecified muscles.

In other embodiments of the foregoing methods, wherein the administration of TT evokes a reversible inhibitory response, the tetanus toxin is administered to other selected sites including tissues or organs of smooth muscles affected by bronchospasm, cricopharyngeal spasm, esophageal spasm, achalasia, obesity, spastic colon or anal fissures. The muscles include pulmonary smooth muscles, cricophalyngeus muscle, esophagus, lower esophager sphincter, stomach wall muscles, colon wall muscles and anal sphincter.

In yet other embodiments of the foregoing methods, tetanus toxin evokes reversible inhibitory responses by administering it at the selected site including tissues or organs affected by gastric acid, prostate hypertrophy, rhinorrhea, salivation, irritation of pulmonary mucosa, psoriasis, immune tolerance or immune reaction. In the foregoing embodiments, the applicable target neurons are part of the autonomic parasympathetic system and include gastric nerve supply, prostate gland, intranasal mucosa, pulmonary mucosa, submandibular gland, skin and thymus. In certain other embodiments of the foregoing methods, other selected sites for TT application include tissues or organs affected by osteoporosis or angina including bones, coronary arteries and cardiac muscles.

In certain other embodiments of each of the foregoing methods TT can be administered with a vasoconstrictor at the target neurons of the selected site in an amount from about 1:200,000 to about 1:100,000. The vasoconstrictor can be administered prior to, contemporaneously with or immediately after the administration of the tetanus toxin. Vasoconstrictors useful in the present invention include without limitation epinephrine, norepinephrine, or epinephryl borate.

In another aspect, the invention is directed to a pharmaceutical formulation for modulating a neural function of an animal at a selected site affected by target neurons, the formulation comprising a therapeutically effective amount of tetanus toxin suspended in a pharmaceutically acceptable carrier for delivery to the selected site, wherein the therapeutically effective amount of tetanus toxin is from about 100 units to 10,000 units for the selected site.

In another aspect, the invention is directed to a pharmaceutical formulation for decreasing the activity of a nerve function in an animal at a selected site, the formulation comprising a therapeutically effective amount of tetanus toxin suspended in a pharmaceutically acceptable carrier for delivery to the selected site, wherein the therapeutically effective amount of tetanus toxin is from about 100 units to 10,000 units for the selected site. In the foregoing embodiment the selected site includes tissues or organs affected by spastic dysphonia, hemifacial spasm and blepharospasm, temporal mandibular join syndrome, bruxism, torticollis, neck pain, writer's cramp, limb muscle contracture, migraine headache, bronchospasm, cricopharyngeal spasm, esophageal spasm, achalasia, obesity, spastic colon, anal fissures, gastric acid, prostate hypertrophy, rhinorrhea, salivation, irritation of pulmonary mucosa, psoriasis, immune tolerance or immune reaction, osteoporosis or angina.

In yet another aspect, the invention relates to a pharmaceutical formulation for increasing the activity of a nerve function in an animal at a selected site, the formulation comprising a therapeutically effective amount of tetanus toxin suspended in a pharmaceutically acceptable carrier for delivery to the selected site wherein the therapeutically effective amount of tetanus toxin is from about 0.001 units to about 2000 units for the selected site. The selected site for the pharmaceutical formulation of this embodiment comprises tissues or organs affected by sleep apnea and snoring, scoliosis, strabismus, muscle atrophy, neurologically impaired muscles including muscular dystrophy, ALS, myasthenia gravis, decrease in muscle mass, decrease in facial muscle tone, nasal congestion, impotence, hair loss or hypotension. Other selected sites for the pharmaceutical formulation of this embodiment include tissues or organs including lower esophageal sphincter, anal sphincter, bladder, vaginal sphincter, pyloric sphincter, upper esophageal sphincter, colon wall muscles. Other selected sites for the pharmaceutical formulation of this embodiment include tissues or organs affecting saliva production or nasal mucosa, the organs affecting saliva production including submandibular gland, parotid gland, sublingual gland, or minor salivary glands of the oral mucosa.

The invention is further directed to the use of tetanus toxin in the preparation of a medicament for a method of treating a clinical disorder or symptom of an animal, comprising administering a therapeutically effective amount of tetanus toxin to a selected site affected by target neurons related to the clinical disorder or symptom of the animal, wherein the therapeutically effective amount of tetanus toxin is from about 100 units to 10,000 units of the selected site.

Another aspect of the invention is directed to the use of tetanus toxin in the preparation of a medicament for a method of treating a clinical disorder or symptom in an animal, comprising administering a therapeutically effective amount of tetanus toxin at a selected site of the animal in order to decrease the activity of a nerve function in the animal, the nerve function related to the clinical disorder or symptom of the animal, wherein the tetanus toxin causes an excitatory or reversible inhibitory response of the nerve function at the selected site innervated by the target neurons, wherein the therapeutically effective amount of tetanus toxin is from about 100 units to 10,000 units of the selected site. In this aspect of the invention, the selected site comprises tissues or organs affected by spastic dysphonia, hemifacial spasm and blepharospasm, temporal mandibular join syndrome, bruxism, torticollis, neck pain, writer's cramp, limb muscle contracture, nerve regeneration within a muscle, migraine headache, bronchospasm, cricopharyngeal spasm, esophageal spasm, achalasia, obesity, spastic colon, anal fissures, gastric acid, prostrate hypertrophy, rhinorrhea, salivation, irritation of pulmonary mucosa, psoriasis, immune tolerance or immune reaction, osteoporosis or angina.

In yet another aspect, the present invention is directed to the use of tetanus toxin in the preparation of a medicament for a method of treating a clinical disorder or symptom in an animal, comprising administering a therapeutically effective amount of tetanus toxin at a selected site of the animal in order to increase the activity of a nerve function in the animal, the nerve function related to the clinical disorder or symptom of the animal, wherein the tetanus toxin causes an excitatory or reversible inhibitory response of the nerve function at the selected site innervated by the target neurons, wherein the therapeutically effective amount of tetanus toxin is from about 0.001 units to about 2000 units for the selected site. In this embodiment of the invention the selected site comprises tissues or organs affected by sleep apnea and snoring, scoliosis, strabismus, muscle atrophy, neurologically impaired muscles including muscular dystrophy, ALS, myasthenia gravis, decrease in muscle mass, decrease in facial muscle tone, nasal congestion, impotence, hair loss or hypotension. Other selected sites for the foregoing embodiment include tissues or organs including lower esophageal sphincter, anal sphincter, bladder, bladder sphincter, vaginal sphincter, pyloric sphincter, upper esophageal sphincter, colon wall muscles. Other selected sites for the foregoing embodiment comprise tissues or organs affecting saliva production or nasal mucosa, the organs affecting saliva production including submandibular gland, parotid gland, sublingual gland, or minor salivary glands of oral mucosa.

Yet another aspect to the invention is directed to a method of modulating a cellular, non-neural activity of an animal at a selected site, the method comprising administering at the selected site a therapeutically effective amount of the tetanus toxin, wherein the cellular activity includes release of a cellular component comprising hormones, inflammatory modulators from nerves or blood cells, cholinergic caused secretions, mucus secretions from respiratory, digestive or urinary glands.

In the foregoing embodiment, the cellular activity occurs in cells including macrophages, monocytes, endocrine cells or renal cells. In this embodiment the cellular activity is modulated over a period from about one hour to about one year. In a preferred embodiment the cellular activity can be controlled or modulated over a period of one week to four months.

In certain embodiments of each of the foregoing methods related to modulating cellular activity, each of the foregoing methods further comprises: (i) determining the level of antibodies of tetanus toxin present in blood plasma of the animal prior to administering of any tetanus toxin; and (ii) immunizing the animal when the level of tetanus toxin is below 0.1 IU/ml. The immunizing is performed passively or actively.

The level of antibodies present in blood plasma is determined by antibody titer.

In certain embodiments of each of the foregoing methods the therapeutically effective amount of tetanus toxin is delivered at the selected site by injection, topical application, aerosol, instillation into ducts or body orifices, encapsulated into liposomes or artificial vesicles with bi-layer lipid membrane. In the foregoing embodiments the therapeutically effective amount of tetanus toxin is suspended in a pharmaceutically acceptable carrier. Additionally, the tetanus toxin can be in the form of a freeze-dried powder.

In the embodiments of the foregoing methods related to modulating cellular activity the therapeutically effective amount of tetanus toxin is from about 0.001 units to about 10,000 units for the selected site.

In other more preferred embodiments of the foregoing methods, the therapeutically effective amount of tetanus toxin is from about 1 unit to about 5000 units for the selected site.

In other most preferred embodiments of the foregoing methods, the therapeutically effective amount of tetanus toxin is from about 10 units to about 1000 units for the selected site.

In certain embodiments of each of the foregoing methods the selected site comprises tissues or organs affected by malignant carcinoma or inflammatory conditions.

In yet another aspect, the invention relates to a pharmaceutical formulation for modulating a cellular activity of cells of an animal, the formulation comprising a therapeutically effective amount of tetanus toxin suspended in a pharmaceutically acceptable carrier for delivery to the selected site, wherein the therapeutically effective amount of tetanus toxin is from about 0.001 units to about 10,000 units for the selected site.

In another more preferred embodiment, the invention relates to the pharmaceutical formulations of the foregoing methods, wherein the therapeutically effective amount of tetanus toxin is from about 1 unit to about 5000 units for the selected site.

In yet another most preferred embodiment, the invention related to the pharmaceutical formulations of the foregoing methods, wherein the therapeutically effective amount of tetanus toxin is from about 10 units to about 1000 units for the selected site.

In certain embodiments of the invention the pharmaceutical formulations are administered at a selected site comprising tissues or organs affected by malignant carcinoma or inflammatory conditions.

Another aspect of the invention is directed to the use of the tetanus toxin in the preparation of a medicament for a method of effectively treating a clinical disorder or symptom in an animal, comprising administering a therapeutically effective amount of tetanus toxin in order to modulate a cellular activity of an animal at a selected site, the cellular activity including release of a cellular component including hormones, inflammatory modulators from nerves or blood cells, cholinergic caused secretions, mucus secretions from respiratory, digestive or urinary glands, wherein the therapeutically effective amount of tetanus toxin is from about 0.001 units to about 10,000 units for the selected site.

In a preferred embodiment the invention is directed to the use of the tetanus toxin in the preparation of a medicament for a method of effectively treating a clinical disorder or symptom in an animal, comprising administering a therapeutically effective amount of tetanus toxin in order to modulate a cellular activity of an animal at a selected site, the cellular activity including release of a cellular component including hormones, inflammatory modulators from nerves or blood cells, cholinergic caused secretions, acid secretions mucus secretions from respiratory, digestive or urinary glands, wherein the therapeutically effective amount of tetanus toxin is from about 1 unit to about 5,000 units for the selected site. In a most preferred embodiment the use of the tetanus toxin is in a therapeutically effective amount from about 10 units to about 1000 units for the selected site. In the foregoing uses of tetanus toxin, the selected site comprises tissues or organs affected by malignant carcinoma or inflammatory conditions.

The invention is also directed to a method for the alleviation of pain experienced by an animal comprising administering tetanus toxin suspended in a pharmaceutically acceptable carrier to a selected site of the animal, the tetanus toxin in a therapeutically effective amount sufficient to decrease or reversibly inhibit the release of inflammatory neurotransmitters or neuropeptides associated with the pain.

In another aspect, the invention relates to a method for the alleviation or blocking of pain sensation experienced by an animal comprising administering tetanus toxin to a selected site of the animal in a therapeutically effective amount sufficient to denervate sensory neurons affecting the release of inflammatory neurotransmitters or neuropeptides controlling the selected site of the animal.

In yet another aspect, the invention is directed to a method for the increase of muscle mass in an animal comprising administering to a selected site of a muscle a pharmaceutically effective amount of tetanus toxin sufficient to cause an increase or an excitatory response in the neural activity of the selected muscle. In the foregoing method the selected muscle is a skeletal or smooth muscle.

These and other advantages of the present invention will be appreciated from the detailed description and examples which are set forth herein. The detailed description and the examples enhance the understanding of the invention, but are not intended to limit the scope of the invention.

DETAILED DESCRIPTION OF THE INVENTION

Methods and pharmaceutical compositions for modulating a neural function of an animal by the administration of an effective amount of tetanus toxin to an animal are provided. These methods and compositions can be used for management or treatment of many clinical disorders or diseases.

As used herein, in the context of modulating or controlling a neural function, a "selected site" is defined to include a tissue or organ affected directly or indirectly by a target neuron. In the context of modulating non-neural, cellular activity, a "selected site" refers to a tissue or organ affected directly or indirectly by a non-neural cellular by including release of a cellular component such as hormones, inflammatory modulators from nerves or blood cells, cholinergic caused secretions, acid secretions, mucus secretions from respiratory, digestive or urinary glands.

As used herein, the term "modulating" is used interchangeably with the term "controlling" and means to adjust to a requirement or regulate.

As used herein, the term "target neurons" refers to a neuron that is affected directly or indirectly by the presence of tetanus toxin in a therapeutically effective amount sufficient to cause a physiological change at the selected site. Target neurons include without limitation neurons functionally clarified as sensory neurons, motor neurons, interneurons, autonomic and central nervous system neurons particularly related to uptake, transport or inhibition of neurotransmitters or neuropeptides.

The term "therapeutically effective amount" means that the tetanus toxin is administered in a non-toxic amount sufficient to cause reduction in the occurrence or magnitude of the symptoms being targeted. When the toxin is used to increase the neuronal tone, a preferred amount may be equal to the amount of botulinum toxin that causes the opposite effect (denervation). When tetanus toxin is used to cause denervation of the target neurons, the amount may be about 500 times greater then the same amount of botulinum toxin required to achieve a similar effect.

As used herein, the term "patient" broadly refers to any animal that is to be treated with the compositions and by the methods herein disclosed. In particular, the disclosed methods and compositions will find use in veterinary practice and animal husbandry for, e.g., birds and mammal, wherever modulation of neural function is convenient or desirable. The term "animal" includes all members of the animal kingdom, including mammals and especially humans.

For purposes of the present invention, tetanus toxin is commercially available from for example, Lederle Laboratories of Wayne, N.J. under the tradename "Tetanus Toxoid Purogenated." The method of the invention will preferably encompass the use of pharmaceutically safe forms of the intact tetanus toxin, including both heavy and light chains, as well as any fragment thereof, such as an AB fragment. Combinations with other moieties such as other proteins including a hybrid of a protein and the heavy or light chain portion of the tetanus toxin are also included in the present invention.

More specifically, for purposes of the present invention, the use of tetanus toxin, as well as a fragment thereof, is contemplated. In addition, it may be beneficial to separate the binding protein portion of the tetanus toxin to use in association with other proteins to allow the other proteins to enter a cell. It may also be beneficial to bind the toxic protein portion of the tetanus toxin to other proteins to allow the toxic protein to enter cells it would otherwise be incapable of entering.

Those of ordinary skill in the art will know, or can readily ascertain, how to obtain tetanus toxins, in a pharmaceutically safe form, preferably, a form that is nonteratogenic. For most of the neurotoxins of the invention, pharmaceutical safety will be dose-dependent such that relatively low dosages of toxin will be "safe" as compared to dosages which are known to be sufficient to produce disease.

Preferably, the tetanus toxins of the invention will be administered as a composition in a pharmaceutically acceptable carrier. To that end, presynaptic neurotoxin compositions are prepared for administration by mixing a toxin of the desired degree of purity with physiologically acceptable sterile carriers. Such carriers will be nontoxic to recipients at the dosages and concentrations employed. Ordinarily, the preparation of such compositions entails combining the neurotoxin with buffers, antioxidants such as ascorbic acid low molecular weight (less than about 10 residues) polypeptides, proteins, amino acids, carbohydrates including glucose or dextrins, chelating agents such as EDTA, glutathione and other stabilizers and excipients. Such compositions may also be lyophilized and will be pharmaceutically acceptable; i.e., suitably prepared and approved for use in the desired application.

Unlike other pharmaceuticals, the biological activity of the same weight of a neurotoxin commonly varies between the different laboratories that produce the toxin. The reason for this is that not all preparations completely remove other proteins or that during isolation of the toxin some molecules tend to lose their biological activity.

Measurement by a biological assay is normally used to obtain a standard preparation of the tetanus toxin. A common biological assay used to measure the toxicity of tetanus toxin is the average dose needed to kill 50% of mice when injected subcutaneously. This amount of toxin is referred to as the mouse $LD_{50}$, or the mMLD (mouse minimum lethal dose), or simply as a unit of tetanus toxin.

Another biological assay commonly used in experimental studies of neurotoxins is the mouse hemi diaphragm preparation (Bulbring, E., J Phys (London), 1, 38-61, (1946)). This is an in vitro assay consisting of half of the diaphragm of a mouse and the nerve that innervates it. The nerve is electrically stimulated to cause the diaphragm to contract and the effect of different toxin preparations on blocking the neuromuscular transmission can be precisely measured. The advantage of this particular assay is that it precisely measures the effect of toxin at the neuromuscular junction, which is the neural connection that is usually of interest to investigators as well as clinicians.

Except for vaccine preparations, tetanus toxin is not used commercially; there is no current standard that composes a unit. Instead, the unit has been reported by Haberman, et al. to vary from 0.3 ng/kg to 25 ng/kg (Habermann, et al., Naunyn Schmiedebergs Arch Pharmacol, 311(1), 33-40, (1980)). The dose of tetanus toxin needed for a local effect will vary depending on the desire for excitatory or inhibitory action, the specific type of neural tissue (Montecucco, C. and G. Schiavo, Q Rev Biophys, 28(4), 423-72 (1995)), the size of the tissue or organ in which the effect is desired, the species to be injected, the activity of the nerve, temperature (Habermann, E., F. Dreyer, and H. Bigalke, Naunyn Schmiedebergs Arch Pharmacol, 311(1), 33-40, (1980)) and other factors.

There is no absolute standard weight that constitutes a unit of tetanus toxin, and as tetanus toxin has never been used for clinical applications there has never been any compelling reason to adopt a standard. In future clinical applications of tetanus toxin a commercial vendor would be required to produce and distribute a standardized and consistent preparation of tetanus toxin in unit dose form. At present there is no standard, and the weight of tetanus toxin constituting a unit that is currently available from different companies or laboratories varies from approximately 0.1 ng to 100 ng, with most being approximately 1 ng. For this reason, as used in the present invention a unit of tetanus toxin means 0.02 ng of tetanus toxin.

In contrast to BT, TT has never been used for clinical applications. This is surprising as TT has a variety of special qualities that makes it potentially much more clinically useful then BT. First, it binds to all classes of neurons: motor, autonomic, and sensory. In contrast the botulinum toxin binds to motor neurons. Secondly, TT is transported to the central nervous system. Although the toxin binds to peripheral nerves, mostly motor neurons, it does not cause its primary effect by intoxicating the peripheral neuron. Instead the toxin is transported within the axons of the motor neurons to their cell bodies located in the spinal column and brain stem. There the motor neurons release the toxin, allowing to pass the synapse and bind and enter into neurons of the central nervous system. Thirdly, it blocks the release of most if not all neurotransmitters: acetylcholine, norepinephrine, epinephrine, dopamine, glutamate, GABA, glycine, serotonin, as well as neuropeptides CGRP, neuropeptide Y, substance P and others; and neuroendocrine hormones oxytocin, vasopressin. In the central nervous system the toxin binds preferentially to neurons that use the neurotransmitters GABA and glycine. After binding the toxin enters into these neurons and blocks the release of these neurotransmitters. The GABA and glycine containing neurons are the inhibitory neurons of the central nervous system. Normally a motor neuron receives input from many inhibitory and excitatory neurons and these opposing influences largely cancel each other. However after inhibitory neurons are blocked the excitatory neurons can stimulate the motor neurons unopposed so that the motor neuron activity increases causing increased activity in the muscle innervated by these intoxicated motor neurons. Clinically this is seen as increased muscle tone that reaches an unremitting spasm in its final stages. Fourthly, TT can cause increased activity of peripheral and central nerves as well as blocking these same nerves depending on the exact dosage used.

The mechanism of action of tetanus toxin is such that the excitatory action evoked by its use is indirect. The tetanus toxin is taken up by a peripheral neuron such as the motor neuron innervating a muscle and is transported back to the cell body of the motor neuron in the spinal column. It is then released into the presynaptic space. Motor neurons are connected to many other neurons that are either excitatory or inhibitory. Under normal circumstances these inputs are balanced so that the motor neuron is excited just enough to perform the appropriate muscle movements. The inhibitory neurons use the neurotransmitters glycine or GABA, and the tetanus toxin binds to and then blocks these neurons (Bigalke, H., et al., Naunyn Schniedebergs Arch. Pharmacol, 316(2), 143-8, (1981)). When the inhibitory neurons are blocked only the excitatory input remains and the activity of the muscle increases.

Each muscle has a different mixture of excitation and inhibition. For example the masseter muscle is a muscle that has a great deal of excitatory input. If tetanus toxin blocks all the inhibitory input to the motor neurons supplying the masseter muscle it goes into an extremely strong and prolonged spasm. This spasm of the masseter muscle clenches the jaw shut and is the origin of the term "lockjaw" that refers to the systemic disease.

In most muscle applications it is not desirable to inject the tetanus toxin to obtain a prolonged spasm. Instead, what is usually needed is a mild to moderate increase in muscle tone. Therefore, very low doses are used for local excitatory applications. For example, when the hind limb of a cat was injected with 1.5 ng into the triceps surae muscle of the hind leg, the tetanus toxin caused an incomplete extension of the leg developed after about one week (Takano, et al., Toxicon 27(4), 431-8, (1989)). When 7.5 ng or more were injected the leg of the cat remained extended in a stiff continuous spasm that the animal could not overcome.

Similarly, excitatory applications in human muscle or other target tissue requires doses in the range of 0.001 to 10 ng depending on the size of the muscle and its underlying neural mixture of excitatory and inhibitory inputs. To achieve the desired application, those skilled in the art understand that it is useful to begin by using a dose at the lower end of the foregoing range and wait to observe the effects. Subsequent increasing doses of tetanus toxin can be given until the proper level is achieved.

Tetanus toxin can also block peripheral neural transmission directly at the neuromuscular junction to cause a flaccid paralysis. Experiments show that this direct neural blocking effect requires approximately 500 times more tetanus toxin than those used to cause excitation (Habermann, E., et al., Naunyn Schmiedebergs Arch Pharmacol, 311(1), 33-40, (1980)). The reason for this large disparity in dosages causing the different effects of excitation or inhibition is unknown.

As local paralysis may require 0.5 to 50 ng of tetanus toxin or more to achieve its effect, these doses approach or exceed the lethal dose for a non-immunized human. The lethal dose for a non-immunized human is approximately 2.5 ng/kg or 175 ng for a 70 kg individual. Therefore use of tetanus toxin for neural block may be restricted to smaller targets requiring low amounts of toxin. It would, therefore, be critical to ascertain the immune status of the human be known prior to administering the tetanus toxin. Universal immunization is performed in the United States and most industrialized nations. Immune status is measured in international units of tetanus antibody. A blood plasma antibody content greater than 0.1 IU/ml is considered protective against systemic tetanus. The level of immune status is high after immunization and gradually falls over in the following years. Studies have shown that half of vaccinated human adults have less then 0.1 IU/ml. Such individuals would probably require booster vaccination to raise their levels of immunity.

Tetanus toxin can also block action potentials in nerve axons just like local anesthetics. As a result, tetanus toxin can be used to inject and block any nerve along its course, thus increasing its clinical usefulness. Unlike botulinum toxin, tetanus toxin binds to the membrane of the neuronal axon (Herreros, et al., European Journal Neurosci 9(12), 2677-86, (1997)). Experimental animal models of local tetanus show large amounts of the toxin along the course of the nerve leading from the injected muscle back to the spinal column outside of the axons (Erdmann, et al., Neuryn Schmiedebergs, Archive of Pharmacology, 290(4), 357-373, (1975)). Physiological studies of patients with local tetanus suggest that the nerve conduction is decreased or blocked, which is a separate effect from the block at synapses, (Dastur, F. D., et al., Journal Of Neurology, Neurosurgery And Psychiatry 40(8), 782-6 (1977)).

Also many of the proposed injections might require the use of electromyography for proper localization within the muscle. This uses the tip of the needle to sense muscle activity and is routine in many botulinum toxin injections.

Unexpectedly large injections of tetanus toxin can be made into a muscle without systemic or regional spread. Partly this is due to extremely high affinity that the tetanus toxin has for the neural membrane that causes it to bind rapidly with neurons (Critchley, D. R., et al., J Cell Biol, 100(5), 1499-507 (1985)). Additional mechanisms can be used to reduce the risk of side effects. An example would be to add adrenaline 1:100,000 dilution, phenylephrine ½% or other vasoconstricting agents to the injection. These would cause a temporary local vasoconstriction and decrease in blood flow, thereby decreasing the opportunity for the tetanus toxin to enter the systemic circulation.

Other vasoconstrictors useful in the present invention include without limitation epinephrine, norepinephrine, or epinephryl borate.

Other additional precautions can be taken to prevent the systemic spread of tetanus toxin when large doses are injected locally. For example, the tetanus anti toxin can be injected, either into the same site as tetanus toxin injection but with some time delay or at a distant site (Fezza, J. P., et al. Opthalmic Plastic and Reconstructive Surgery, 16(2), 101-113, (2000)). In the rabbit the lethal dose of tetanus toxin in a typical 2 kg rabbit is approximately 1-10 ng or 0.5-5 ng/kg. However, an injection of 25 ng, 2,500 to 25,000 times the lethal dose, was injected safely into the orbicularis oculi muscle. In this experiment 250 IU of tetanus antitoxin were simultaneously injected intramuscularly into a hind limb muscle and blocked any systemic spread. At five days these animals demonstrated paresis of the injected eyelid without any local or systemic spread of toxicity. Clearly this is at the highest end of dosage, spectrum as either reducing the amount of tetanus toxin to 125 IU, or increasing the injected dose of tetanus toxin to 37.5 ng, resulted in local or systemic signs of toxicity (Fezza, J. P., et al., Opthalmic Plastic and Reconstructive Surgery, 16(2), 101-113, (2000)).

In certain preferred embodiments, the tetanus toxin is used to control motor neuron function. For example, the toxin is administered locally to a particular target site in the body (e.g., particular muscles) in a sufficient amount to increase the neural activity of the motor neurons in the target area. This in turn increases neural stimulation of muscle cells innervated by said neurons. This results in increased muscle tone, and if the muscle is immobilized in a shortened length, it will rapidly adapt to the shortened length (Abe, Y., et aL., Acta Otolaryngol (Stockh), 112 (4), 703-9, (1992)). Alternatively, by adjusting the amount of the tetanus toxin, one may produce an opposite effect, e.g., denervation of the neurons. For a clinically beneficial effect, a therapeutically effective amount of the tetanus toxin is administered.

In preferred embodiments, low concentrations of tetanus toxin to increase tone are administered to genioglossus, geniohyoid and soft palate muscles (e.g., for treatment of sleep apnea); pharyngeal muscles, to aid swallowing in patients with dysphagia; paraspinal muscle (e.g., for treatment of scoliosis); extraocular muscle (e.g., for treatment of strabismus); muscles in the immobilized limb (e.g., to prevent atrophy during long-term casting); to different muscle in paralytic neurological diseases such as ALS to restore muscle tone; lower esophageal sphincter (e.g., to control esophageal reflux); stomach muscle (e.g., for gastric contracture and decreased appetite); facial muscles (e.g., for increased tone and youthful appearance); target muscles to increase muscle mass as a substitute for exercise.

In other preferred embodiments high concentrations of tetanus toxin to decrease tone are administered to facial muscles to decrease facial muscle or eyelid spasm; to temporal muscles to treat myofascial pain and headache; to cervical muscles, to treat torticollis and cervical dystonia; various target muscles for muscular dystrophy, ALS, myasthenia gravis; limb muscles (e.g., to treat spasm or contracture resulting from upper motor neuron lesions, such as seen after strokes); to jaw muscles to decrease bruxism; to laryngeal muscles to treat spasmodic dysphonia and hyperfunctional conditions; to forearm muscles to treat writers cramp; to leg muscles to treat night cramps; in any muscle where increased branching of motor nerves is beneficial such as during nerve regeneration after traumatic nerve injury.

In certain embodiments, the tetanus toxin may be administered locally to a particular part of the autonomic system (e.g., target tissue or organ) to control the activity of the neurons in that area, which also in turn affects the target autonomic system innervated by said neurons.

In certain embodiments, the tetanus toxin is administered locally to a target autonomic system (e.g., tissue or gland) in a therapeutically beneficial low amount sufficient to increase the activity of the neurons in that area. This results in increased stimulation of the cells (e.g., of tissue or gland) innervated by said neurons. Tetanus toxin may be administered to salivary, lacrimal and vaginal glands to treat dry mouth, dry eye and atrophic vaginitis; to mammary glands to increase milk production; to nasal mucosa to treat nasal congestion and allergic symptoms; to penile vasculature tissue to prolong erections and treat impotence; to pancreas and other endocrine glands to increase hormone production; to colon and other gastrointestinal organs to increase motility to treat constipation; to sympathetic nerves of the lung to relax smooth muscle in asthma and chronic obstructive diseases; to gastric smooth muscle to cause gastric shrinkage and cause feelings of satiety to decrease appetite and cause weight loss; to pulmonary mucus glands to increase serous mucous production and cilia transport to treat cystic fibrosis; to adipose tissue to cause lipolysis and fat cell shrinkage.

In certain other embodiments, higher doses may be used to decrease autonomic neural activity. When used clinically, the tetanus toxin is administered in a therapeutically effective amount to hair follicles to treat hair loss; to prostate glands to cause shrinkage of an enlarged prostate; to connective tissue to increase its metabolism to treat the lax skin of the aged; to pain fibers to decrease pain sensation and inflammation; to skin in proliferative or allergic diseases such as psoriasis and atopic dermatitis; to sebaceous glands of skin to treat acne; to sebaceous glands of ear canal skin to decrease ear wax; to sympathetic nerves of the circulatory system to decrease blood pressure; to neuromodulate the immune response in the thymus and spleen, lymph nodes, or any tissue where neural immune interactions exist; to skin, digestive tract or mucosa to prevent recognition of foreign antigens to produce tolerance; to tonsils to decrease their size; to the anterior chamber of the eye to decrease fluid production to treat ocular hypertension; to gastric mucosa to decrease acid production in reflux esophagi is; to the nasal mucosa to decrease rhinorrhea, and to decrease the neural influence on mast cell histamine release to decrease allergic symptoms; to pterygopalatine ganglia to block vasodilatory neurons to prevent true migraine headache.

In certain preferred embodiments, the tetanus toxin is administered to the target autonomic system in a therapeutically effective amount to treat nasal congestion rhinorrhea and allergic symptoms (Ado, A. D., Elksperimentalnaia I Klinicheskaia Farniakologiia, 58 (3), 43-5 (1995); Albegger, K., Hno, 36 (10), 389-98 (1988); Agro, A. et al., Advances In Neuroimmunology, 5 (3), 311-9, (1995)) modulate immune responses (Ado, A. D., Vestnik Rossiiskoi Akadenii Meditsinskikh Nauk, (7), 48-51 (1993); Albanese, A., et al., Mov Disord, 12(5), 764-6, (1997)), relax anal sphincters in constipation (Sabbadini, E. et al., Neuroimmunomodulation, 2 (4), 184-202, (1995)) affect penile erection, decrease inflammation and pain in various organs, decrease skin proliferation in diseases such as psoriasis, invoke antigen tolerance, decrease blood pressure, decrease migraine headache, increase or decrease salivation, decrease sweating, decrease the size of the prostate gland, increase the connective tissues, and control hair loss.

In certain other embodiments, the tetanus toxin is administered to sensory neurons to cause a reversible sensory block. One application of such use would be to block pain from any part of the body, e.g., by locally administering to that part an amount effective to block or decrease the pain. Another embodiment would be to block the inflammatory mediators released by sensory neurons, e.g., by locally administering to a joint a therapeutic beneficial amount in rheumatoid arthritis.

In certain other embodiments tetanus toxin is applied to parts of the central nervous system, either directly or as a result of retrograde transport from a peripheral nerve.

In certain other embodiments tetanus toxin is administered to non-neuronal cells for beneficial effect. These include macrophages and other white blood cells to decrease inflammation, endocrine cells to decrease the secretion of hormones, parietal cells of the stomach to decrease acid production, fluid producing cells in the eye to decrease intraocular pressure in glaucoma, malignant cells to decrease motility and metastases.

The present invention is also directed to veterinary uses of tetanus toxin, e.g., to increase the muscle mass of a target veterinary animal. This includes milk and meat production.

According to the present invention, tetanus toxin may be administered by variety of modes of administration. When administered locally, the mode of administration includes but is not limited to injection (including pressure jet injectors), aerosolized (for nasal, upper airway or lung administration), topical application (on skin and mucous membranes and on internal body surfaces (such as during surgery or in the treatment of trauma) open wounds, and by instillation into ducts (salivary, mammary, lacrimal) or body orifices (urethra, anus, oral).

When administered locally to a particular target site, the tetanus toxin affects the activity of the neurons in that area, preferably without having a systemic effect. As tetanus toxin is taken up by axons it can be administered along the course of a nerve to block or increase the neural activity received by a distant organ or tissue innervated by the nerve. In preferred embodiments, the tetanus toxin is administered locally to a target site in the body. However, in certain cases, local application can deliberately result in a wide distribution of the toxin. For example, the local application can be to the cerebrospinal fluid, so that it is distributed to large parts of the central nervous system; or into an artery to be distributed to the body part that the artery perfuses. In certain embodiments, application of the tetanus toxin may be systemic, e.g., into the systemic circulation so that there is distribution throughout the body.

Local application of tetanus toxin at pharmacological levels causes their uptake by local nerve endings and their retrograde transport to the central nervous system (CNS). In local application encompassing all means of delivery, including but not limited to injection, e.g., pressure jet injectors, and topical application. In the CNS the tetanus toxin is transported transynaptically and binds to inhibitory neurons. The result is the disinhibition of the peripheral neuron and an increase in its activity. The exact amount of the increase and its pattern is related to the biology of that particular neuron. For widespread distribution in the CNS such as the veterinary applications the toxin can be directly injected into the cerebrospinal fluid.

When the toxin is to be administered to cells that lack the necessary membrane receptors, the toxin may be encapsulated into liposomes, artificial vesicles with bi-layer lipid membranes. The vesicles would merge with cells in the area of injection and deliver the toxin internally. To increase specificity the surface of the liposomes can be coated with specific proteins such as antibodies or glycoproteins that allow specific docking of the liposome to the target cell.

EXAMPLES

The invention is further described in the following examples. The examples are illustrative of some of the products and methods of making the same falling within the scope of the present invention. They are, of course, not to be considered in any way restrictive of the scope of the invention. Numerous changes and modification can be made with respect to the invention. The materials used in the examples hereinbelow are readily commercially available.

Excitatory intramuscular applications of tetanus toxin are illustrated in examples 1-18. Inhibitory responses elicited by application of tetanus toxin are illustrated in examples 19 to 37. Increased tone in the nerves of the autonomic system is desirable in many conditions. The mechanism of action is similar to that observed in muscles. Retrograde transport from the site of injection causes block of inhibitory afferent input. Examples 30, 33 and 38 illustrate the use of tetanus toxin to modulate or control cellular activity of holocrine secretions endocrine cells and macrophages.

Example 1

Sleep Apnea and Snoring

In this example, a 60 year old male with snoring and obstructive sleep apnea is injected with tetanus toxin by passing a needle through the mucosa in the floor of the mouth. 1 unit of tetanus toxin is injected into both genioglossus muscles. The needle is advanced further until the geniohyoid muscle is entered and a further 1 unit is injected into each muscle. The needle is removed and reinserted through the oral mucosa of the soft palate within 2 centimeters of the edge of the hard palate. 1 unit of tetanus toxin is injected into each levator muscle. Within one week the incidence of snoring and obstruction during sleep decreases.

Sleep apnea and snoring are clinical conditions affecting genioglossus and/or geniohyoid, tensor and levator veli palatini muscles. Sleep apnea is a common disorder in which soft tissue of the upper airway (tongue and soft palate) impede the flow of air during inspiration thereby causing a partial obstruction to airflow and vibration of the soft tissue of the area (snoring) or complete obstruction to airflow. The result of the obstruction includes disturbed sleep patterns, snoring, daytime somnolence, difficulty in concentrating, and contributes to mood depression, hypertension and cardiac disease. The pathophysiology of obstructive sleep apnea includes a decrease in activity of the genioglossus and other upper airway muscles. The genioglossus muscle inserts into the base of the tongue and has phasic activity synchronous with inspiration that moves the tongue forward to dilate the airway. The geniohyoid inserts into the hyoid bone and has a similar inspiratory activity. The tensor and levator veli palatini also have inspiratory activity that moves the soft palate superiorly. In this embodiment, administration (e.g., injections) of 1 unit of tetanus toxin into the genioglossus and/or geniohyoid, tensor and levator veli palatini muscles can result in increased amplitude of the phasic motions and decrease the airway obstruction.

Example 2

Scoliosis—Paraspinal Muscle

A female patient age 10 suffering from scoliosis, curvature of the spine, is treated by injection of 100 units of tetanus toxin into paraspinal muscles. In 1-3 days the patient shows increased tone in muscles that serve to straighten the spine.

The developmental misalignment of the spine that occurs with scoliosis could be corrected with administration (e.g., injections) of tetanus toxin into the proper muscles that would straighten the spine. This remodeling of a bone by long-term increase in muscular activity has numerous other applications. Other examples include obtaining an excitatory response from craniofacial muscles in order to rearrange the facial skeleton.

Example 3

Strabismus

A male patient age 5, suffering from strabismus, or improper alignment of the eyes, is treated by injection of 0.1 unit of tetanus toxin into the medial rectus muscle of the misaligned eye. In 1 to 3 days the eye moves into alignment. This example illustrates concept similar to that described in Example 2 except that rearrangement occurs in the muscular soft tissue. Administration (e.g., injections) of tetanus toxin into the lateral rectus or other appropriate muscle increases its tonic activity and causes a straightening of the alignment of the globe.

Example 4

Preventing Muscle Atrophy

A male patient age 25 is suffering from a fracture of the femur and is scheduled to have a leg cast placed for 6 weeks. 10 units of tetanus toxin is injected into each muscle of the thigh. After 1 to 3 days the tone of the immobilized muscles increases. After 6 weeks the cast is removed and the muscles show less atrophy then expected.

After a severe bone fracture or ligament tear, casting and immobilization can result in atrophy of the muscles of the immobilized limbs. This undesirable side effect is prevented by the administration (e.g., via injection) of tetanus toxin into the muscles prior to casting to increase their tone and prevent atrophy.

Example 5

Esophageal Reflux—Lower Esophageal Sphincter

In the lower esophageal sphincter, a 50 year old male with afflicted with reflux esophagitis is injected with 1 unit of tetanus toxin. In 3 days the symptoms of reflux acidity decrease.

Laxity in the lower esophageal sphincter results in reflux of acid contents up the esophagus. This common medical problem can be prevented by administration (e.g., injection) of tetanus toxin into the lower esophageal sphincter. This example demonstrates that the increase of tone prevents esophagial reflux from occurring.

Example 6

Bladder or Bowel Incontinence—Sphincters

A 50 year old female having urinary incontinence is injected with 1 unit of tetanus toxin into the external (pudendal nerves) and internal (sympathetic axons from the inferior mesenteric ganglion) urethral sphincters. In 3 days increased muscle tone in these sphincters relieves the urinary incontinence.

In a related example, a 50 year old male with urinary incontinence is injected with 1 unit of tetanus toxin into the urinary sphincter under direct vision using a cystoscope. In 1-3 days the symptoms of urinary continence improve.

Many medical conditions result in incontinence, the inability to contain urine or bowel contents. In those cases where decreased tone of the sphincter is the problem, administration (e.g., injections) of the tetanus toxin into the sphincter can increase tone. Additional sphincters that could be injected include the vaginal introitus, pyloric sphincter, and upper esophageal sphincter.

Example 7

Gastric Contracture and Decreased Appetite

A 40 year old female suffering from obesity is injected with 100 units of tetanus toxin into the smooth muscle of the stomach wall and/or pyloric sphincter under direct vision using an endoscope. After 1 to 3 days she feels more satiated and her appetite decreases.

It is known that the feeling of satiety is at least partly due to distension of the stomach. Some surgical procedures have been designed to take advantage of the effect by surgically decreasing the size of the stomach. Instead, administration (e.g., injections) of tetanus toxin can be made into the stomach wall. The increased tone induced in the innervation of the stomach smooth muscle would, over time, decrease its size. The effect is a feeling of satiety after smaller amounts of food intake.

Example 8

Muscular Dystrophy, ALS, Myasthenia Gravis

Many neurological disorders and aging are associated with a decrease in the efferent activity to muscles. So long as a minimum number of motor axons are still present, this activity can be increased with administration (e.g., injections) of tetanus toxin. The particular muscle is dependent on the conditions of the disease but includes all skeletal muscles.

Example 9

Muscle Contracture

A 60 year old female is suffering from spastic contraction of her right arm after a cerebral vascular accident is injected with 10 units of tetanus toxin into the triceps muscle of the right arm. After 1-3 days the symptoms of contracture decrease and the arm rests in a more extended position.

Contracture, stroke and other upper motor neuron lesions result in a disinhibition of limb muscles and especially the flexors of the upper limb and the extensors of the lower. Administration (e.g., injections) of tetanus toxin can increase tone in the muscle opposite to the contracture and result in a more neutral position of the limb.

Example 10

Facial Muscle Tone

Each orbicularis oculi muscle of a 70 year old female patient is injected with a total of 1 unit of tetanus toxin in divided doses. In 3 days the tone of the muscle improves and the tissue laxity around the eyes decreases.

This example illustrates that the administration of tetanus toxin to facial muscle increases the tone and youthful appearance of the patient. A youthful appearance is due in part to good tone in facial muscles. In the aged this tone could be improved by administration (e.g., via direct injection) into the facial muscle. The muscles most likely to benefit from this treatment useful are the smile muscles rhizorius and quadratus and the periorbital muscles. Increased tone in these muscles flatten the redundant folds of skin seen in aging and are used largely as a substitute for a blepharoplasty.

Example 11

Increased Muscle Mass as a Substitute for Exercise

A 25 year old weight lifter has 10 units of tetanus toxin injected into both biceps. In 1-3 days the tone of the biceps muscles increases. In 1 to 6 weeks the mass and strength of the muscle increases.

Increases in muscle tone and/or mass is generally desirable for cosmetic, competitive, preventative or rehabilitative reasons. Those who desire the effects of exercise would undergo injection into the muscle of interest such as the biceps strictly for the purpose of increasing tone and causing hypertrophy. In competitive athletes the same method can be used for a functional effect. An example might be a weightlifter with a relative weakness in certain arm muscles that cannot be corrected with normal exercise and could be benited by undergoing a tetanus toxin injections. In certain conditions the effect of increased tone are both cosmetic and medically desirable. One example is the muscle of the abdominal wall. Weak muscles of the abdominal wall allow sagging of the abdomen and also predispose the patient to back injury. Injection of tetanus toxin into the abdominal muscles increases the tone of the abdominal wall causing it to flatten and help with spinal alignment.

Example 12

Pharyngeal Paresis with Dysphagia

A 60 year old female suffering from dysphagia after a cerebrovascular accident is injected with 1 unit of tetanus toxin into the inferior and middle constrictor muscles after 1-3 days the symptoms of dysphagia improve.

Example 13

Nasal Decongestion—Nasal Mucosa

In this example, a 20 year old male with nasal congestion due to perenial allergic rhinitis is injected with 1 unit of tetanus toxin into the mucosa covering each turbinate. After one week there is a noticeable decrease in congestion.

Nasal congestion is the major symptom of allergic and infectious rhinitis and is one of the most common complaints in all of medicine. The mucosa covering the intranasal turbinates is capable of changing thickness partly as a result of changes in blood flow. The mechanism of decongestion involves increased activity of the sympathetic nervous system. Specifically, increased tone in sympathetic nerves to the nasal mucosa contracts smooth muscle in arterioles and venules and shrinks the mucosa.

This example illustrates that administration (e.g., injections) of tetanus toxin into the nasal mucosa causes nasal decongestion.

Example 14

Penile Erections and Ejaculation

A 40 year old male with impotence due to a diabetic neuropathy is injected with 1 unit of tetanus toxin into the base of the penis causing increased neural activity in the autonomic nerves as well as the pudendal motor nerves to the ischiocavemosis and bulbospongiosis muscle. In one week the patient can maintain an erection when aroused.

The control of the penile function is a complex mixture of both parasympathetic and sympathetic innervation. Cholinergic sympathetic nerves from the sacral plexus cause the vasodilation enabling erections. Adrenergic sympathetic neurons activate the smooth muscle of the vas deferens and seminal vesicles. Emission of ejaculate is a sympathetic response. Secretions of the bulbourethral and prostate are under parasympathetic control. Autonomic dysfunction from a variety of medical reasons can cause impotence.

It is apparent from this example that the application of tetanus toxin to control the activity of the appropriate autonomic sympathetic nerves results in the desired result.

Example 15

Increased Connective Tissue

A 70 year old female is injected with a total of 1 unit of tetanus toxin delivered in four separate injections to various quadrants of the skin of the face. Increased neural activity results in a thicker dermal layer to the skin and a more youthful appearance.

Connective tissue is formed by fibroblasts or myofibroblasts. It is known that denervation of the motor and nerve supply to an area of skin causes a significant decrease in skin thickness. The activity of the nerve supply to skin apparently simulates the production of connective tissue.

This example demonstrates that tetanus toxin can be applied (e.g., by injection) to the dermal layer of the skin to increase connective tissues, resulting in a more youthful appearance.

Example 16

Hair Loss

A fifty year old male with male pattern baldness is injected in the bald area of the scalp with multiple injections of 0.25 unit of tetanus toxin. In one month the patient notes early hair regrowth in the area.

Hair loss appears to be in part due to decreased activity of the autonomic innervation to hair follicles. Experiments in rats show that anagen (hair growth) is associated with increased sympathetic activity within the nerves surrounding the hair follicle. It is seen that administration (e.g., injections) of tetanus toxin into the skin in areas of hair loss increases autonomic activity and slows or reverses hair loss.

Example 17

Veterinary Uses of Tetanus Toxin

Cattle, goats, sheep, lamb, pigs, poultry, fish, invertebrates and other animals are all raised and harvested for their meat. In most cases the important meat harvested from these animals is muscle. Increased muscle size translates into increased meat production. In this embodiment tetanus toxin would be administered (e.g., injection) to animals to cause muscular hypertrophy.

In one example the pectoralis muscle of the turkey is increased by applying an injection of 1 unit of tetanus toxoid into each pectoralis muscle of the turkey. After 2 days muscle tone would increase in the muscles and the mass of the muscle would increase.

A cow undergoes a lumbar puncture and 1 unit of tetanus toxin is instilled into the cerebrospinal fluid. The next day the animal exhibits mildly increased tone of all muscles. Over the next two months the muscle mass of the low increases by 10%.

Example 18

Increase in Milk Production

Milk is another product that is harvested from animals. Milk production is largely hormonal but there is evidence that the nervous system plays a large role in secretion of milk and plays a role in production.

Direct administration (e.g., injection) into the mammary gland or retrograde administration (e.g., injection) through its duct can result in increased neural activity and such increase translates into increased milk production.

A dairy cow has injected into each teat 1 unit of tetanus toxin. In 2 days the tone of the smooth muscle within the teat increases and the quantity of milk produced increases.

Example 19

Sweating—Skin

Sweating, also called hyperhydrosis, is under the control of the sympathetic nervous system but the neurotransmitter used by the post ganglionic neuron is acetytlcholine. The locations of clinical important sweating include the armpit; the feet (the humidity causes the fungal infection of athlete's foot); the genital area (crotch itch); the palms and the brow.

In one example, a forty year male experiencing excessive sweating from the axillae is injected in this area with 1000 units of tetanus toxin. Decrease in sweating is noted within 3 days.

This example illustrates that an anticholinergic medication such as tetanus toxin is capable of blocking the production of sweat.

Example 20

Rhinorrhea (Post Nasal Drip)—Nasal Mucosa

Rhinorrhea is the production of excessive secretions from the nose and is a major symptom of allergic, infectious and vasomotor rhinitis. Anticholinergic medication is effective for blocking rhinorrhea for brief periods or injected into the intranasal turbinates of humans. The parasympathetic ganglia that contains the postganglionic cell bodies that supply the nasal secretory glands is in the pterygopalatine ganglia.

In one example, a 70 year old female complains of profuse watery rhinorrhea throughout the day. Injections of 500 units of tetanus toxin are made into both inferior turbinates with decreased rhinorrhea in 3 days.

In another example, a 50 year old male complains of perennial allergies and profuse nasal mucus rhinorrhea. A needle is passed from the oral side of the hard palate through the pterygopalatine canal and into the pterygopalatine space and 500 units of tetanus toxin are injected on each side. The symptoms of rhinorrhea improve within 3 days from treatment with tetanus toxin.

Thus, blocking cholinergic neural transmission in the pterygopalatine ganglia by using tetanus toxin is also effective at decreasing rhinorrhea.

Example 21

Prostatic Hypertrophy—Prostate Gland

A 60 year old male with difficulty voiding due to prostatic hypertrophy is injected with 500 units of tetanus toxin into the prostate gland. Over the month following the injection with tetanus toxin the patient notices gradual decrease in his symptoms.

Prostatic hypertrophy is common in males over 50 years of age and causes difficulties in initiating urination. It has long been known that denervation of the autonomic innervation of the gland causes it to decrease in size.

This example demonstrates that injections of tetanus toxin into the prostate gland causes it to shrink.

Example 22

Asthma, COPD—Pulmonary Mucus Secretion

A 60 year old male patient with bronchitis has the symptoms of excessive pulmonary mucus. 5000 units of tetanus toxin are mixed with 10 cc of normal saline and aerosolized and inhaled by the patient over a 30 minute period. In 2 days the patient notes a decrease in mucus production.

A prominent symptom of many lung diseases is the production of excessive amounts of mucus. These diseases include asthma, chronic obstructive pulmonary disease, bronchitis, bronchiectasis and cystic fibrosis. Pulmonary mucus is produced by small glands within the respiratory mucosa covering the bronchi.

This example illustrates that mucus production is controlled by application of tetanus toxin to inhibit parasympathetic neural activity of pulmonary mucosa.

Example 23

Asthma, COPD—Bronchial Smooth Muscle

Many lung diseases have the symptom of chronic or acute airway obstruction. The lumem of bronchioles is largely controlled by contraction of smooth muscle that is under parasympathetic control.

A 13 year girl with asthma is placed under light anesthesia and a brochoscope is inserted trough the mouth and into the trachea. Using a thin gauge transbronchial needle 20 injections of 100 units each of tetanus toxin are made through the mucosa. In the following weeks the symptom of bronchospasm is improved. This example illustrates that transmucosal absorption or injection of tetanus toxin through the mucosa blocks parasympathetic activity and prevents bronchospasm.

Example 24

Salivation—Parotid, Submaxillary and Sublingual Lands

Many neurologically impaired patients have difficulty preventing saliva from entering their lungs. Contamination of the lungs with the bacteria laden saliva can lead to a lethal pneumonia.

A 60 year old female with amyotrophic lateral sclerosis has been aspirating saliva. The patient has 100 units of tetanus toxin injected into each of the three major salivary glands bilaterally for a total dose of 600 units. In two days salivation has decreased considerably and she no longer aspirates saliva. Thus, salivation is under parasympathetic control and the amount of salivation has been shown to decrease when both animals and humans are injected with tetanus toxin.

Example 25

Sphincters—Anal Fissures and Constipation

Increased tone in the anal sphincter causing constipation is called outlet obstruction and occurs in Parkinson disease as well as other neurological conditions.

A 65 year old male patient with Parkinson's disease and associated paradoxical activation of the puborectalis muscle during straining is treated with an injection of a total of 1000 units of tetanus toxin into two sites of the puborectalis muscle. Within 3 days the patient experiences a decline in straining pressure during evacuation.

Chronic anal fissure is maintained by contraction of the internal anal sphincter. Surgical sectioning of the sphincter is successful in 85% to 95% of patients however permanently weakens the sphincter and may cause anal deformity and incontinence.

In another example, a 35 year old female with a chronic anal fissure is injected with a total of 1000 units into two sites of the anal sphincter. In 1-3 days tone of the anal sphincter decreases and the fissure heals over the following 2 months.

From these examples, it is apparent that injections of botulinum toxincon successfully be used to relax the anal sphincter and allow it to heal.

Example 26

Achalasia—Lower Esophageal Sphincter

Increased contraction tone of the cholinergic innervation of the lower esophageal sphincter can interfere with swallowing.

A 40 year old male has achalasia of the esophagus with severe difficulties in swallowing. A flexible endoscope is passed into the esophagus and 300 units of tetanus toxin are injected transmucossally into the lower esophageal sphincter. In 3 days the patient notices improvement in swallowing.

It is shown that this condition can be successfully treated with transmucosal injections of tetanus toxin.

Example 27

Obesity—Gastric Wall Muscle

A 30 year old female has a flexible endoscope passed through the esophagus and into the stomach. The antral wall muscle of the stomach is injected with 1000 units of tetanus toxin. After 1 week the food consumption of the patient decreases and she begins to lose weight.

The feeling of hunger and satiation are partly related to the state of contraction of the stomach wall. The paralysis of the gastric antrum slows the emptying of the stomach and causes feeling of early satiety. It is therefore, shows that patients with morbid obesity can benefit from endoscopic injections of tetanus toxin into the stomach wall.

Example 28

Immune Tolerance

It has been shown that blocking the parasympathetic nerves to an area of skin (or mucosa) followed by injection of antigen into the area invokes immune tolerance to the antigen. Administration (e.g., injections) of tetanus toxin followed by the antigen can induce tolerance to the antigen. This effect can be used to treat or ameliorate autoimmune disorders.

Autoimmune diseases with their putative antigenic proteins set forth parenthetically include without limitations: experimental autoimmune encephelomyelitism (myelin basic protein); arthritis (type II collagen); uveitis (S-antigen, interphotoreceptor binding protein); diabetes (insulin, glutamine decarboxylase); myasthenia gravis (acetylcholine receptor); thyroiditis (thyroglobulin); and multiple sclerosis (myelin).

A forty year old female with multiple sclerosis is injected with 1000 units of tetanus toxin into the skin of the left forearm. One week later myelin is injected into the same site. Within a month the patient exhibits a decrease in symptoms.

Another area in which immune tolerance is beneficial is organ transplantation. Humans normally develop an immune reaction to the foreign proteins, especially major histocompatibility protein, that is present on the surface of the cells in the transplanted organ.

In another example pertaining to organ transplantation, a 40 year old female requiring a kidney transplant is injected with 1000 units of tetanus toxin into the skin of the left arm. After one week cell surface antigens from a potential donor are injected into the same area. In one month the patient is tested for tolerance by injection of the same cell surface antigens into the skin of the right forearm. No noticeable reaction indicates that tolerance has been achieved and the transplant can be done.

Thus, administration of tetanus toxin into a region of (e.g., injections) allows subsequent presentation of an antigen to invoke tolerance to that antigen. This effect could be beneficial to patients with autoimmune disease or potential recipients of allografts or xenograft organs.

Example 29

Gastric Acid

Gastric acid production is under the control of the parasympathetic nerves. However, an additional method of blocking the acid production is in the parietal cells that produce the acid. They secrete $H^+$ by vesicle release and can be blocked directly (Alexander et al., American Journal of Physiology, 273 (6 Pt. 2), F 1054-7, (1997)). A third method is to block the hormones that increase acid production, secretin and gastrin. An additional beneficial effect would be to block the production of the enzyme trypsin.

Example 30

Holocrine Secretion

Holocrine glands are a class of skin secretory glands that produce a lipid secretion and are partly under neural control. Holocrine glands include sebaceous and follicular glands, cerumen glands and mammary glands. Blocking the neural input to these glands by administration (e.g., injection) of tetanus toxin may be useful in a variety of medical conditions, examples include acne where over production of secretion is the basis for the inflammation and infection.

Also cerumen overproduction is one of the most common reasons for visits to otolaryngologists. Administration (e.g., injection) to the skin of the ear canal would block cerumen production and prevent ear wax accumulation in the ear canal.

In addition, the tetanus toxin may be used to block the activity of the sebaceous glands, thereby providing beneficial effects in the skin condition acne.

Example 31

Skin Disorders

Psoriasis, atopic dermatitis (hives), vitiligo are all related to parasympathetic activity. It has long been known that denervation of an area of skin causes resolution of these skin disorders in the denervated area. Administration of the tetanus toxin (e.g., by injection) into affected areas can block the activity and cause improvement or resolution of the symptoms. Skin injections with tetanus toxin can decrease of the skin disorders listed above by decreasing the parasympathetic activity at selected sites.

Example 32

Migraine

Administration of the tetanus toxin (e.g., by injection) into the pterygopalatine ganglia would block postganglionic nerves to the carotid artery and thereby block the arterial spasms caused by these nerves that is the basis for migraine headaches. Migraine like tension headaches could be treated by injection into the temporalis muscle.

Example 33

Adipose Tissue

Glucose uptake by adipose tissue is necessary for lipid production. Tetanus toxin delivered by liposomes blocks lipid glucose uptake by fat cells and can cause a decrease in their size. The cellular activity of other endocrine cells can be inhibited by administration (via injection) of tetanus toxin. Endocrine cells affected by treatment with tetanus toxin include thyroid, pancreatic and tumor cells.

Example 34

Vomeronasal Organ

The vomeronasal organ senses pheromones and plays a role in reproductive behavior and other autonomic drives. Administration (e.g., injection) of tetanus toxin into this organ can block, or increase these drives.

Example 35

Immune System T Cell Maturation and Release

Parasympathetic activity is related to maturation and release of T cells from the thymus and spleen. T cells are the cellular mediators of antigen recognition. Increased parasympathetic activity increases the maturation and release of T cells; the opposite occurs when these organs are acutely denervated. Administration (e.g., injection) of tetanus toxin into the thymus and/or spleen at various doses can either increase or decrease the release of T cells.

A 25 year old patient with HIV and low T cell counts is injected with 100 unit of tetanus into his thymus gland. After 1 week T cell levels in the blood increase.

A 50 year old female with multiple sclerosis has an acute worsening of her disease and is injected with 100 units into her thymus gland. One week after the injection the symptoms are ameliorated.

Example 36

Sensory Uses of Tetanus Toxin

Unlike botulinum, tetanus toxin has been shown to bind and enter sensory nerves, undergo retrograde transport and cause anesthesia. These observations have been made in experimental animals as well as in clinical tetanus. In addition to the decrease in afferent neural activity the tetanus toxin would block the release of inflammatory mediators from the sensory nerve (substance p, neuropeptide Y, CGRP) as these neuropeptides are by SNARE mechanism using the protein VAMP that is inactivated by tetanus toxin. The most important use for this effect can be to block pain from any part of the body. For example, chronic joint pain can be blocked by administration of the tetanus toxin (e.g., by injection) into the joint bursa.

A 75 year old female with a degenerative right hip joint with chronic pain undergoes an injection of 1000 units of tetanus toxin into the joint. Within one week the pain of the patient has decreased. The above example illustrates that the specific target of administration can vary with a specific clinical condition but can include bone, cartilage, ligament, muscle, fascia, mucosa, skin, pleural membranes, epineurium, synovial membranes, neuromas, and smooth muscle.

Another use for sensory blockade is the axon-axonal reflexes underlying inflammation. Sensory axons react to noxious stimuli by evoking a reflex vasodilation in the entire region innervated by the nerve (sometimes referred to as the wheal and flair reaction). Tetanus toxin can block the release of the neuropeptides that evoke this reflex.

A 65 year old male with chronic bronchitis and the symptoms of excess mucus production and paraoxysmal coughing inhales an aerosolized solution of 1000 units of tetanus toxin for 30 minutes. Two days later his coughing decreases.

The above examples show that another use for sensory blockade can be in the chronic cough, mucus production and bronchospasm initiated by intra pulmonary sensory receptors. In this embodiment the tetanus toxin is best delivered by inhaled aerosol.

Example 37

Cardiovascular System

The cardiovascular system, the heart, arteries, and veins have extensive autonomic innervation. In the heart sympathetic activity causes increased heart rate and contractile force. Parasympathetic stimulation slows the heart and decreases contractile force. The rate of cardiac contraction is controlled by the sinoatrial node, a small ganglia in the right atrium of the heart, while the propagation of the contraction from atria to ventricles is controlled by the atriaventricular node (AV) node.

Cardiac disorders which can be treated with tetanus toxin pharmaceutical formulations include the cardiac arrythmias: tachycardia, bradycardia, and ventricular fibrillation. Additional disorders include coronary spasm resulting in angina and/or myocardial infarction. Catherization of the coronary arteries allows release of tetanus toxin into the blood perfusing the ventricles and the particular coronary artery used allows some localized distribution of the toxin to areas of the heart most affected. In these cases inhibitory doses of tetanus toxin can decrease cardiac excitability by inhibiting sympathetic stimulation and by a direct effect on cardiac myocytes. Injection of tetanus toxin into coronary arteries at the higher inhibitory doses results in decreased sympathetic activation of the smooth muscle and decreases the intensity of coronary artery spasm ameliorating angina. Injection of tetanus toxin into the sinoatrial (SA) node at excitatory levels can increase parasympathetic activity and slow the heart rate decreasing the possibility of arrhythmia and/or angina. The use of catherization techniques that reach the above mentioned areas of the heart are well known to those skilled in the art and do not require undue experimentation.

Example 38

White Blood Cells

Monocytes and macrophages have receptors that allow uptake and internalization of tetanus toxin. Once internalized the toxin disrupts the molecular mechanism underlying cellular mobility as well as secretion of vesicles. Many inflammatory processes are associated with the migration of macrophages or to the area. Once in the region of inflammation these cells release other cytokines that increase inflammation or cause tissue breakdown. Administration of tetanus toxin can slow or stop the migration of macrophages as well as prevent the release of inflammatory mediators from cells in the area. Tetanus toxin is also capable of blocking the aggregation and secretion of neutrophils but requires of vector like liposomes for cell internalization. Rheumatoid arthritis is an example of a disorder that can benefit from this therapy, with administration directly into the synovial bursa. This is an example of using tetanus toxin to control cellular activity of specific target cells such as macrophages.

Thus, while there have been described what are presently believed to be the preferred embodiments of the present invention, those skilled in the art will appreciate that other and further modifications and changes can be made without departing from the true spirit of the invention, and it is intended to include all further and other such modifications and changes which come within the scope of the invention as set forth in the appended claims.

What is claimed is:

1. A method of administering a therapeutically effective amount of tetanus toxin to a selected site, having target neurons whose activity is reversibly affectable thereby, of an animal in need of modulation of activity of said neurons, comprising the initial steps, prior to said administration, of
   a) determining the level of antibodies to tetanus toxin present in the blood plasma of said animal,
   b) immunizing the animal where the level of antibodies to tetanus toxin is below 0.1 IU/ml and,
   c) administering a therapeutically effective amount of tetanus toxin to a selected site,
   whereby the neurotoxin reversibly modulates the activity of the target neurons.

2. The method of claim 1, wherein the therapeutically effective amount of tetanus toxin causes a decrease in neural activity or reversible inhibitory response of the neural activity at the selected site.

3. The method of claim 1, wherein the therapeutically effective amount of tetanus toxin causes an increase in neural activity or an excitatory response of the neural activity at the selected site.

4. The method of claim 1 comprising administering to a selected site affecting target neurons of an animal an amount of tetanus toxin sufficient to cause a denervation of the target neurons, wherein the denervation results in reversible inhibitory response of the nerve function at the selected site innervated by the target neurons.

5. The method of claim 3, comprising administering to a selected site affecting target neurons of an animal an amount of tetanus toxin sufficient to cause an excitatory response of the nerve function at the selected site affected by the target neurons.

6. The method of claim 1, wherein the therapeutically effective amount of tetanus toxin is delivered at the selected site by injection, topical application, aerosol, or instillation into ducts or body orifices.

7. The method of claim 4, wherein the therapeutically effective amount is from about 100 units to about 5000 units for the selected site.

8. The method of claim 7, wherein the therapeutically effective amount is from about 1000 units to about 2000 units for the selected site.

9. The method of claim 5, wherein the therapeutically effective amount is from about 0.001 units to about 2000 units for the selected site.

10. The method of claim 9, wherein the therapeutically effective amount is from about 2 units to about 4 units for the selected site.

11. The method of claim 5, wherein the selected site comprises tissues or organs affected by sleep apnea and snoring, dysphagia, scoliosis, strabismus, muscle atrophy, tissues or organs affecting salivary gland secretions, vaginal secretions, lacrimal secretions, mammary secretions tissues or organs affected by nasal congestion, impotence, hair loss, connective tissue of lax, aged skin or hypotension and neurologically impaired muscles affected by muscular dystrophy, amyotrophic lateral sclerosis or myasthenia gravis, decrease in muscle mass, or decrease in facial muscle tone.

12. The method of claim 5, wherein the selected site comprises vascular, pulmonary, genitourinary or gastrointestinal smooth muscle, the lower esophageal sphincter, anal sphincter, bladder wall, bladder and urethral sphincter, vaginal sphincter, stomach wall, pyloric sphincter, upper esophageal sphincter, and colon wall muscles.

13. The method of claim 11, wherein the organs affecting saliva production include submandibular gland, parotid gland, sublingual gland, or minor salivary glands of the oral mucosa.

14. The method of claim 4, wherein the selected site comprises tissues or organs contributing to a symptom of spastic dysphonia, hemifacial spasm and blepharospasm, temporal mandibular joint syndrome or bruxism, torticollis, neck pain, writer's cramp, limb muscle contracture, nerve regeneration within a muscle, migraine headache, allergy, asthma COPD, bronchitis, bronchospasm, cricopharyngeal spasm, esophageal spasm, achalasia, obesity, spastic colon or anal fissures, gastric acid, prostate hypertrophy, rhinorrhea, salivation, irritation of pulmonary mucosa, psoriasis, acne, sweating, immune tolerance or immune reaction, osteoporosis, coronary artery spasm or angina.

15. The method of claim 4, wherein the selected site comprises hair follicles, prostate gland, connective tissue of lax, aged skin, inflamed fibers, skin in proliferative or allergic diseases, sebaceous glands, sweat glands, sympathetic nerves affecting the circulatory system, neurons controlling an immune response in thymus, lymph nodes, or tissue having a neural immune interaction, skin, digestive tract, tonsils, anterior chamber of the eye, gastric mucosa, nasal mucosa or pterygopalatine ganglia.

16. A method comprising administering at a selected site in an animal, a therapeutically and modulatorily effective amount of tetanus toxin,
   comprising the initial steps, prior to said administration, of
   a) determining the level of antibodies to tetanus toxin present in the blood plasma of said animal and
   b) immunizing the animal where the level of tetanus toxin is below 0.1 IU/ml
   whereby the cellular activity of said animal at said site is modulated wherein said cellular activity includes release of a cellular component comprising hormones, growth factors, inflammatory modulators from nerves or immune cells and blood cells, cholinergic secretions, mucus secretions from respiratory, digestive or urinary glands.

17. The method of claim 16, wherein the cellular activity occurs in cells including macrophages, monocytes, neutrophils, endocrine cells or renal cells.

18. The method of claim 16, wherein the cellular activity is modulated over a period from about one hour to about one year.

19. The method of claim 16, wherein the therapeutically effective amount of tetanus toxin is delivered at the selected site by injection, topical application, aerosol, instillation into ducts or body orifices, encapsulated into liposomes or artificial vesicles with bi-layer lipid membrane.

20. The method of claim 16, wherein the therapeutically effective amount of tetanus toxin is from about 0.001 units to about −5000 units.

21. The method of claim 16, wherein the therapeutically effective amount of tetanus toxin is from about 10 units to about 1000 units.

22. The method of claim 16, wherein the selected site comprises tissues or organs affected by malignant carcinoma or inflammatory conditions.

23. A pharmaceutical formulation in dosage form for modulating a cellular activity of cells of an animal, comprising a therapeutically effective amount of tetanus toxin in a pharmaceutically acceptable carrier wherein the dosage comprises from about 0.001 units to about 5000 units of tetanus toxin.

24. The pharmaceutical formulation of claim 23, wherein the dosage comprises from about 10 units to about 1000 units of Tetanus toxin.

25. A method of preventing the transmission of pain sensation in an animal from a selected site on said animal to the central nervous system comprising
   a) determining the level of antibodies to tetanus toxin present in the blood plasma of said animal and
   b) immunizing said animal where the level of tetanus toxin is below 0.1 IU/ml and
   c) administering to a selected site in said animal, tetanus toxin in a therapeutically effective amount sufficient to decrease or reversibly inhibit the release of inflammatory neurotransmitters or neuropeptides associated with the pain whereby transmission of pain sensation from the selected site to the central nervous system is prevented.

26. A method of preventing the transmission of pain sensation in an animal from a selected site on said animal to the central nervous system comprising
   a) determining the level of antibodies to tetanus toxin present in the blood plasma of said animal and
   b) immunizing said animal where the level of tetanus toxin is below 0.1 IU/ml and
   c) administering to a selected site in said animal a therapeutically effective amount of tetanus toxin sufficient to decrease the function of sensory neurons, the release or binding of inflammatory neurotransmitters or neuropeptides associated with the pain whereby transmission of pain sensation from the selected site is prevented.

27. The method of claim 1 wherein a fragment of tetanus toxin is used alone, where that fragment is the light chain of tetanus toxin or the fragment is combined with a second protein or other molecule or delivered via liposomes.

28. The method of claim 1 wherein the therapeutically effective amount of tetanus toxin causes a modulation of neural activity at a site other than the selected site.

29. The method of claim 28 where the selected site is the vomeronasal organ.

30. The method of claim 1 wherein the therapeutically effective amount of tetanus toxin invokes immune tolerance to autoimmune antigens or antigens of a transplanted organ.

* * * * *